(12) United States Patent
Kusumoto (10) Patent No.: US 11,406,451 B2
(45) Date of Patent: Aug. 9, 2022

(54) ULTRASOUND THERMOMETRY FOR ESOPHAGEAL OR OTHER TISSUE PROTECTION DURING ABLATION

(71) Applicant: Walter Kusumoto, Chico, CA (US)

(72) Inventor: Walter Kusumoto, Chico, CA (US)

( * ) Notice: Subject to any disclaimer, the term of this patent is extended or adjusted under 35 U.S.C. 154(b) by 94 days.

(21) Appl. No.: 16/285,622

(22) Filed: Feb. 26, 2019

(65) Prior Publication Data

US 2019/0262074 A1 Aug. 29, 2019

Related U.S. Application Data

(60) Provisional application No. 62/735,571, filed on Sep. 24, 2018, provisional application No. 62/723,366, (Continued)

(51) Int. Cl.
*A61B 18/24* (2006.01)
*A61B 8/12* (2006.01)
(Continued)

(52) U.S. Cl.
CPC .............. *A61B 18/24* (2013.01); *A61B 5/015* (2013.01); *A61B 8/12* (2013.01); *A61B 8/5207* (2013.01);
(Continued)

(58) Field of Classification Search
CPC ......... A61B 18/24; A61B 8/12; A61B 8/5207; A61B 5/015; A61B 18/1492;
(Continued)

(56) References Cited

U.S. PATENT DOCUMENTS 5,078,717 A   1/1992 Parins
8,825,144 B2  9/2014 Starks
(Continued)

FOREIGN PATENT DOCUMENTS

WO    WO 2018/060502    4/2018

OTHER PUBLICATIONS

Alvarenga AV, Teixeira CA, Ruano MG, Pereira WCA. Influence of temperature variations on the entropy and correlation of the Grey-Level Co-occurrence Matrix from B-Mode images. Ultrasonics. Feb. 2010;50(2):290-3.
(Continued)

*Primary Examiner* — Rex R Holmes
(74) *Attorney, Agent, or Firm* — Heisler & Associates (57) ABSTRACT

During an ablation procedure, such as ablation of the left ventricle of the heart, thermal damage to adjacent structures is avoided by this method. An ultrasound probe is placed within the esophagus near the left atrium, or placed at other locations sufficiently close to the ablation site to image tissues to be protected from excessively high (or low) thermal energy during ablation. The ultrasound probe reflected signal gathered by a sensor thereof is analyzed. Using one or more algorithms, this signal analysis identifies changes in speed of sound of transmitted and received sound waves and correlates the speed of sound changes to changes in temperature of the associated tissues and the result is displayed. Such ultrasound thermometry is used to monitor temperature of tissues surrounding the ablation site to minimize potential for thermal damage thereto. The method also evaluates motion occurring near the ablation site, correcting for such motion.

22 Claims, 7 Drawing Sheets

Related U.S. Application Data filed on Aug. 27, 2018, provisional application No. 62/635,770, filed on Feb. 27, 2018.

(51) Int. Cl.

| | |
|---|---|
| A61B 8/08 | (2006.01) |
| A61B 5/01 | (2006.01) |
| A61B 18/14 | (2006.01) |
| A61B 18/08 | (2006.01) |
| A61B 18/02 | (2006.01) |
| A61B 18/00 | (2006.01) |

(52) U.S. Cl.
CPC ............ *A61B 18/02* (2013.01); *A61B 18/082* (2013.01); *A61B 18/1492* (2013.01); *A61B 2018/00351* (2013.01); *A61B 2018/00577* (2013.01); *A61B 2018/00642* (2013.01); *A61B 2018/00672* (2013.01); *A61B 2018/00702* (2013.01); *A61B 2018/00791* (2013.01); *A61B 2018/0212* (2013.01)

(58) Field of Classification Search
CPC .................. A61B 18/082; A61B 18/02; A61B 2018/00351; A61B 2018/00577; A61B 2018/00791; A61B 2018/00642; A61B 2018/00702; A61B 2018/00672; A61B 2018/0212; A61B 2018/00666; A61B 2017/00106; A61B 8/466; A61B 8/4254; A61B 8/085; A61B 8/0883; A61B 8/546; A61B 5/0095; A61B 5/7246; A61B 5/0035; A61B 5/0422; A61B 5/063; A61B 5/064; A61B 5/0036; A61B 5/0044; A61B 5/6852; A61B 2018/00994

See application file for complete search history.

(56) References Cited

U.S. PATENT DOCUMENTS

| | | | |
|---|---|---|---|
| 2008/0132792 A1 | 6/2008 | Rosemberg | |
| 2009/0312637 A1 | 12/2009 | Raju | |
| 2013/0296845 A1 | 11/2013 | Bar-Tal | |
| 2015/0320481 A1* | 11/2015 | Cosman, Jr ............ | A61B 34/10 606/35 |
| 2016/0228175 A1 | 8/2016 | Sliwa | |
| 2017/0079625 A1 | 3/2017 | Wang | |
| 2017/0100091 A1* | 4/2017 | Eigil .................... | A61B 8/5238 |
| 2017/0296217 A1 | 10/2017 | Hissong et al. | |

OTHER PUBLICATIONS

Alvarenga AV, Teixeira CA, Ruano MG, Pereira WCA. Evaluation of the influence of large temperature variations on the grey level content of B-Mode images. Physcs Proc. 2010;3(1):415-9.
Amini AN, Ebbini ES, Georgiou TT. Noninvasive estimation of tissue temperature via high-resolution spectral analysis techniques. Biomedical Engineering, IEEE Transactions on. 2005;52(2):221-8.
Anand A, Byrd L, Kaczkowski PJ, editors. In situ thermal parameter estimation for HIFU therapy planning and treatment monitoring; Ultrasonics Symposium, 2004 IEEE; Aug. 23-27, 2004; 2004.
Anand A, Kaczkowski PJ. Noninvasive Determination of in Situ Heating Rate Using Khz Acoustic Emissions and Focused Ultrasound. Ultrasound in Medicine and Biology. Oct. 2009;35(10):1662-71.
Anand A, Kaczkowski PJ. Noninvasive Measurement of Local Thermal Diffusivity Using Backscattered Ultrasound and Focused Ultrasound Heating. Ultrasound in Med. & Biol., vol. 34, No. 9, pp. 1449-1464, 2008.
Anand A, Savery D, Hall C. Three-dimensional spatial and temporal temperature imaging in gel phantoms using backscattered ultrasound. Ultrasonics, Ferroelectrics, and Frequency Control, IEEE Transactions on. 2007;54(1):23-31.
Andre M, Wiskin J, Borup D, Johnson S, Ojeda-Fournier H, Olson L. Quantitative Volumetric Breast Imaging with 3D Inverse Scatter Computed Tomography. Ieee Eng Med Bio. 2012:1110-3.
Arthur RM, Basu D, Yuzheng G, Trobaugh JW, Moros EG. 3-D in vitro estimation of temperature using the change in backscattered ultrasonic energy. Ultrasonics, Ferroelectrics, and Frequency Control, IEEE Transactions on. 2010;57(8):1724-33.
Arthur RM, Trobaugh JW, Straube WL, Moros EG. Temperature dependence of ultrasonic backscattered energy in motion-compensated images. IEEE Trans Ultrason Ferroelectr Freq Control. Oct. 2005;52(10):1644-52.
Basarab-Horwath I, Dorozhevets MM, editors. Measurement of the temperature distribution in fluids using ultrasonic tomography; Ultrasonics Symposium, 1994 Proceedings, 1994 IEEE; Oct. 31, 1994-Nov. 3, 1994.1994.
Bayat M, Ballard JR, Ebbini ES. Adaptive motion compensation for in vivo ultrasound temperature estimation. 2013 Joint UFFC, EFTF and PFM Symposium.
Bayat M., Ballard, JR, Ebbini ES. In Vivo Ultrasound Thermography in Presence of Temperature Heterogeneity and Natural Motions. IEEE Trans Biomed Eng. Feb. 2015; vol. 62: 450-457.
Bayat M, Ballard JR, Ebbini ES. Ultrasound Thermography in Vivo: A new model for calculation of temperature change in the presence of temperature heterogeneity. 2013 Joint UFFC, EFTF and PFM Symposium.
Berkovich AE, Smirnov EM, Yukhnev AD, Gataulin YA, Sinitsyna DE, Tarkhov DA. Development of Ultrasound Thermometry Technique Using Tissue-Mimicking Phantom. IOP Conf. Series: Journal of Physics: Conf. Series 1044 (2018).
Bharat S, Techavipoo U, Kiss MZ, Liu W, Varghese T. Monitoring stiffness changes in lesions after radiofrequency ablation at different temperatures and durations of ablation. Ultrasound in Medicine and Biology. Mar. 2005;31(3):415-22.
Casper A, Dalong L, Ebbini ES. Realtime Control of Multiple-focus Phased Array Heating Patterns Based on Noninvasive Ultrasound Thermography. Biomedical Engineering, IEEE Transactions on. 2012;59(1):95-105.
Casper AJ, Dalong L, Ballard JR, Ebbini ES. Real-Time Implementation of a Dual-Mode Ultrasound Array System: In Vivo Results. Biomedical Engineering, IEEE Transactions on. 2013;60(10):2751-9.
Chen BT, Shieh J, Huang CW, Chen WS, Chen SR, Chen CS. Ultrasound thermal mapping based on a hybrid method combining physical and statistical models. Ultrasound Med Biol. Jan. 2014;40(1):115-29.
Chitnis PV, Brecht HP, Su R, Oraevsky AA. Feasibility of optoacoustic visualization of high-intensity focused ultrasound-induced thermal lesions in live tissue. Journal of Biomedical Optics. Mar.-Apr. 2010;15(2).
Civale J, Rivens I, Ter Haar G, Morris H, Coussios C, Friend P, et al. Calibration of ultrasound backscatter temperature imaging for high-intensity focused ultrasound treatment planning. Ultrasound Med Biol. Sep. 2013;39(9):1596-612.
Coviello C, Coussios CC, Passive acoustic mapping of stable and inertial caviation during ultrasound therapy. The Journal of the Acoustical Society of America 136, 2300 (2014).
Coviello C, Faragher SR, Coussios CC. Robust Capon beamforming for passive cavitation mapping during high-intensity focused ultrasound therapy. The Journal of the Acoustical Society of America 128, 2280 (2010).
Curiel L, Chopra R, Hynynen K. In Vivo Monitoring of Focused Ultrasound Surgery Using Local Harmonic Motion. Ultrasound in Medicine and Biology. Jan. 2009;35(1):65-78.
Curiel L, Hynynen K. Localized harmonic motion imaging for focused ultrasound surgery targeting. Ultrasound Med Biol. Aug. 2011;37(8):1230-9.
Dalong L, Ebbini ES. Real-Time 2-D Temperature Imaging Using Ultrasound. Biomedical Engineering, IEEE Transactions on. 2010;57(1):12-6.
Daoud MI, Mousavi P, Imani F, Rohling R, Abolmaesumi P. Tissue Classification Using Ultrasound-Induced Variations in Acoustic (56) References Cited

OTHER PUBLICATIONS

Backscattering Features. IEEE Transactions on Biomedical Engineering, vol. 60, No. 2, Feb. 2013.
Ebbini ES, Simon C, Liu D. Real-Time Ultrasound Thermography and Thermometry, IEEE Signal Process Mag. Mar. 2018; 35(2): 166-174.
Faragher S, Gyöngy M, Hodnett M, Shaw A, Coussios CC. Development of a tomographic cavitation sensor for quality assessment of clinical high intensity focused ultrasound systems. The Journal of the Acoustical Society of America. 2009;125(4):2742.
Fully CH, Clement GT. Ultrasound Phase Contrast Thermal Imaging with Reflex Transmission Imaging Methods in Tissue Phantoms. Ultrasound in Medicine and Biology. Dec. 2009;35(12):1995-2006.
Foiret J, Ferrara KW (2015) Spatial and Temporal Control of Hyperthermia Using Real Time Ultrasonic Thermal Strain Imaging with Motion Compensation, Phantom Study. PLoS ONE 10(8): e0134938.
Fuhrmann TA, Georg O, Haller J, Jenderka KV, Wilkens V. Uncertainty estimation for temperature measurement with diagnostic ultrasound. Journal of Therapeutic Ultrasound (2016).
Ghoshal G, Luchies AC, Blue JP, Oelze ML. Temperature dependent ultrasonic characterization of biological media. J Acoust Soc Am. Oct. 2011;130(4):2203-11.
Gyongy M, Coussios CC. Passive Spatial Mapping of Inertial Cavitation During HIFU Exposure. Ieee T Bio-Med Eng. Jan. 2010;57(1):48-56.
Gyongy M, Coussios CC. Passive cavitation mapping for localization and tracking of bubble dynamics. J Acoust Soc Am. Oct. 2010;128(4):E175-E80.
Gyongy M, Coviello CM. Passive cavitation mapping with temporal sparsity constraint. J Acoust Soc Am. Nov. 2011;130(5):3489-97.
Haworth KJ, Mast TD, Radhakrishnan K, Burgess MT, Kopechek JA, Huang SL, et al. Passive imaging with pulsed ultrasound insonations. J Acoust Soc Am. Jul. 2012;132(1):544-53.
Hsiao, Y.-S., & Deng, C. X. (2016). Calibration and Evaluation of Ultrasound Thermography using Infrared Imaging. Ultrasound in Medicine & Biology, 42(2), 503-517.
Huang CW, Lien DH, Chen BT, Shieh J, Tsui PH, Chen CS, et al. Ultrasound thermal mapping based on a hybrid method combining cross-correlation and zero-crossing tracking. J Acoust Soc Am. Aug. 2013;134(2):1530-40.
Huang SW, Kim K, Witte RS, Olafsson R, O'Donnell M. Inducing and Imaging thermal strain using a single ultrasound linear array. Ieee T Ultrason Ferr. Sep. 2007;54(9):1718-20.
Hussain A, Daoudi K, Hondebrink E, Steenbergen W. Mapping optical fluence variations in highly scattering media by measuring ultrasonically modulated backscattered light. Journal of Biomedical Optics 19(6), Jun. 2014.
Jones RM, O'Reilly MA, Hynynen K. Passive mapping of acoustic sources within the human skull cavity with a hemispherical sparse array using computed tomography-based aberration corrections. The Journal of the Acoustical Society of America. 2014;135(4):2208-9.
Kallel F, Stafford RJ, Price RE, Righetti R, Ophir J, Hazle JD. The feasibility of elastographic visualization of HIFU-induced thermal lesions in soft tissues. Ultrasound in Medicine and Biology. May 1999;25(4):641-7.
Kaluzynski K, Chen X, Emelianov SY, Skovoroda AR, O'Donnel M. Strain Rate Imaging Using Two-Dimensional Speckle Tracking. IEEE Transactions on Ultrasonics, Ferroelectrics and Frequency Control, vol. 48, No. 4, Jul. 2001.
Ke H, Tai S, Wang LV. Photoacoustic thermography of tissue. J Biomed Opt. Feb. 2014;19(2):026003.
Kim Y, Audigier C, Ellens N, Boctor EM. Low-cost Ultrasound Thermometry for HIFU Therapy Using CNN. Johns Hopkins University.
Konofagou EE, Hynynen K. Localized harmonic motion imaging: theory, simulations and experiments. Ultrasound Med Biol. Oct. 2003;29(10):1405-13.
Konofagou EE, Thierman J, Karjalainen T, Hynynen K. The temperature dependence of ultrasound-stimulated acoustic emission. Ultrasound in Medicine and Biology. Mar. 2002;28(3):331-8.
Lai CY, Kruse DE, Caskey CF, Stephens DN, Sutcliffe PL, Ferrara KW. Noninvasive thermometry assisted by a dual-function ultrasound transducer for mild hyperthermia. IEEE Trans Ultrason Ferroelectr Freq Control. Dec. 2010;57(12):2671-84.
Lewis MA, Staruch RM, Chopra R. Thermometry and Ablation Monitoring with Ultrasound. Int J Hyperthermia. Mar. 2015; 31(2): 163-181.
Liu HL, Li ML, Shih TC, Huang SM, Lu IY, Lin DY, et al. Instantaneous frequency-based ultrasonic temperature estimation during focused ultrasound thermal therapy. Ultrasound Med Biol. Oct. 2009;35(10):1647-61.
Liu Y-D, Li Q, Zhou Z, Yeah Y-W, Chang C-C, Lee C-Y, et al. (2017) Adaptive ultrasound temperature imaging for monitoring radiofrequency ablation. PLoS ONE 12(8): e0182457.
Maass-Moreno R, Damianou CA. Noninvasive temperature estimation in tissue via ultrasound echo-shifts. Part I. Analytical model. J Acoust Soc Am. Oct. 1996;100(4 Pt 1):2514-21.
Maass-Moreno R, Damianou CA, Sanghvi NT. Noninvasive temperature estimation in tissue via ultrasound echo-shifts. Part II. In vitro study. J Acoust Soc Am. Oct. 1996;100(4 Pt 1):2522-30.
Maleke C, Konofagou EE. An All-Ultrasound System for Sonication and Real-Time Monitoring of Temperature and Ablation. 2006 IEEE Ultrasonic Symposium.
Maleke C, Konofagou EE. In vivo feasibility of real-time monitoring of focused ultrasound surgery (FUS) using harmonic motion imaging (HMI) IEEE Trans Biomed. Eng. Jan. 2010;57(1):7-11.
Malyarenko EV, Heyman JS, Chen-Mayer HH, Tosh RE. High-resolution ultrasonic thermometer for radiation dosimetry. J Acoust Soc Am. Dec. 2008;124(6):3481-90.
Mast TD, Salgaonkar VA, Karunakaran C, Besse JA, Datta S, Holland CK. Acoustic emissions during 3.1 MHz ultrasound bulk ablation in vitro. Ultrasound in Medicine and Biology. Sep. 2008;34(9):1434-48.
Mehrabani BM, Tavakoli V, Abolhassani MD, Alirezaie J, Ahmadian A. An Efficient Temperature Estimation Using Optical-Flow in Ultrasound B-Mode Digital Images. IEEE Eng Med Bio. 2008:86-9.
Miller NR, Bamber JC, Meaney PM. Fundamental limitations of noninvasive temperature imaging by means of ultrasound echo strain estimation. Ultrasound in Medicine and Biology. Oct. 2002;28(10):1319-33.
Miller NR, Bograchev KM, Bamber JC. Ultrasonic temperature imaging for guiding focused ultrasound surgery: Effect of angle between imaging beam and therapy beam. Ultrasound in Medicine and Biology. Mar. 2005;31(3):401-13.
Miller NR, Bamber JC, Ter Haar GR. Imaging of Temperature-Induced Echo Strain: Preliminary in Vitro Study to Assess Feasibility for Guiding Focused Ultrasound Surgery. Ultrasound in Medicine and Biology, vol. 30, No. 3, pp. 345-356, 2004.
Pernot M, Tanter M, Bercoff J, Waters KR, Fink M. Temperature estimation using ultrasonic spatial compound imaging. IEEE T Ultrason Ferr. May 2004;51(5):606-15.
Pouch AM, Cary TW, Schultz SM, Sehgal CM. In vivo noninvasive temperature measurement by B-mode ultrasound imaging. J Ultrasound Med. Nov. 2010;29(11):1595-606.
Pramanik M, Wang LV. Thermoacoustic and photoacoustic sensing of temperature. J Biomed Opt. Sep.-Oct. 2009;14(5):054024.
Righetti R, Kallel F, Stafford RJ, Price RE, Krouskop TA, Hazle JD, et al. Elastographic characterization of HIFU-induced lesions in canine livers. Ultrasound in Medicine and Biology. Sep. 1999;25(7):1099-113.
Salgaonkar VA, Datta S, Holland CK, Mast TD. Passive cavitation imaging with ultrasound arrays. The Journal of the Acoustical Society of America. 2009;126(6):3071-83.
Seip R, VanBaren P, Cain CA, Ebbini ES. Noninvasive real-time multipoint temperature control for ultrasound phased array treatments. IEEE Trans Ultrason Ferroelectr Freq Control. 1996;43(6):1063-1073.
Seo CH, Shi Y, Huang SW, Kim K, O'Donnell M. Thermal strain imaging: a review. Interface Focus. Aug. 6, 2011;1(4):649-64.

(56) References Cited

OTHER PUBLICATIONS

Seo J, Kim S, Kim Y, Bang W, Choi K, Kong D. Motion Compensation for Ultrasound Thermal Imaging using Motion-mapped Reference Model: an in vivo Mouse Study. Biomedical Engineering, IEEE Transactions on. 2014;(99):1.
Sethuraman S, Anand A, Li JB. Ultrasound Thermometry and Multiphysics Modeling for Liver RF Ablation Monitoring: Ex Vivo Studies. 2014 IEEE International Ultrasonics Symposium Proceedings.
Shah J, Aglyamov SR, Sokolov K, Milner TE, Emelianov SY. Ultrasound imaging to monitor photothermal therapy—Feasibility study. Opt Express. Mar. 17, 2008;16(6):3776-85.
Shah J, Park S, Aglyamov S, Larson T, Ma L, Sokolov K, et al. Photoacoustic imaging and temperature measurement for photothermal cancer therapy. Journal of Biomedical Optics. May-Jun. 2008;13(3).
Shahmirzadi D, Hou GY, Chen J, Konofagou EE. Ex Vivo characterization of canine liver tissue viscoelasticity after high-intensity focused ultrasound ablation. Ultrasound Med Biol. Feb. 2014;40(2):341-50.
Shankar PM. Ultrasonic tissue characterization using a generalized Nakagami model. IEEE T Ultrason Ferr. Nov. 2001;48(6):1716-20.
Shankar PM. A general statistical model for ultrasonic backscattering from tissues. IEEE transactions on ultrasonics, ferroelectrics, and frequency control. 2000;47(3):727-36.
Shankar PM. Quantitative Measures of Boundary and Contrast Enhancement in Speckle Reduction in Ultrasonic B-Mode Images Using Spatial Bessel Filters. IEEE Transactions on Ultrasonics, Ferroelectrics and Frequency Control, vol. 56, No. 10, Oct. 2009.
Simon C, Vanbaren P, Ebbini ES. Two-dimensional temperature estimation using diagnostic ultrasound. IEEE Trans Ultrason Ferroelectr Freq Control. 1998;45(4):1088-1099.
Simon C, VanBaren P, Ebbini E. Quantitative Analysis and Applications of Non-Invasive Temperature Estimation Using Diagnostic Ultrasound. 1997 IEEE Ultrasonics Symposium.
Souchon R, Bouchoux G, Maciejko E, Lafon C, Cathignol D, Bertrand M, et al. Monitoring the formation of thermal lesions with heat-induced echo-strain imaging: A feasibility study. Ultrasound in Medicine and Biology. Feb. 2005;31(2):251-9.
Srinivasan S, Righetti R, Ophir J. Trade-offs between the axial resolution and the signal-to-noise ratio in elastography. Ultrasound Med Biol. Jun. 2003;29(6):847-66.
Stafford RJ, Kallel F, Price RE, Cromeens DM, Krouskop TA, Hazle JD, et al. Elastographic imaging of thermal lesions in soft tissue: A preliminary study in vitro. Ultrasound in Medicine and Biology. Nov. 1998;24(9):1449-58.
Subramanian S, Rudich SM, Alqadah A, Karunakaran CP, Rao MB, Mast TD. In Vivo Thermal Ablation Monitoring Using Ultrasound Echo Decorrelation Imaging. Ultrasound in Medicine and Biology. Jan. 2014;40(1):102-14.
Sumi C, Ichiki Y, Kanai H, editors. Monitoring of the effectiveness of the interstitial RF electromagnetic wave thermal therapy by shear modulus reconstruction; Ultrasonics Symposium, 2000 IEEE; Oct 2000.2000.
Teixeira CA, Alvarenga AV, Cortela G, von Kruger MA, Pereira WC. Feasibility of non-invasive temperature estimation by the assessment of the average gray-level content of B-mode images. Ultrasonics. Aug. 2014;54(6):1692-702.
Teixeira CA, Ruano MG, Ruano AE, Pereira WC. Neuro-genetic non-invasive temperature estimation: intensity and spatial prediction. Artif Intell Med. Jun. 2008.;43(2):127-39.
Teixeira CA, Ruano MG, Ruano AE, Pereira WCA. A Soft-Computing Methodology for Noninvasive Time-Spatial Temperature Estimation. Biomedical Engineering, IEEE Transactions on. 2008;55(2):572-80.
Teixeira CA, Pereira WC, Ruano AE, Ruano MG. On the possiblity of non-invasive multilayer temperature estimation using soft-computing methods. Ultrasonics. Jan. 2010;50(1):32-43.
Trobaugh JW, Arthur RM, Straube WL, Moros EG. A simulation model for ultrasonic temperature imaging using change in backscattered energy. Ultrasound in Medicine and Biology. Feb. 2008;34(2):289-98.
Tsui PH, Chien YT, Liu HL, Shu YC, Chen WS. Using ultrasound CBE imaging without echo shift compensation for temperature estimation. Ultrasonics. Sep. 2012;52(7):925-35.
Varghese T, Zagzebski JA, Chen Q, Techavipoo U, Frank G, Johnson C, et al. Ultrasound monitoring of temperature change during radiofrequency ablation: Preliminary in-vivo results. Ultrasound in Medicine and Biology. Mar. 2002;28(3):321-9.
Wiskin J, Borup D, Andre M, Johnson S, Greenleaf J, Parisky Y, et al. Three-dimensional nonlinear inverse scattering: Quantitative transmission algorithms, refraction corrected reflection, scanner design, and clinical results. The Journal of the Acoustical Society of America. 2013;133(5):3229.
Wiskin J, Borup DT, Johnson SA, Berggren M. Non-linear inverse scattering: High resolution quantitative breast tissue tomography. J Acoust Soc Am. May 2012;131(5):3802-13.
Wu F, Wang ZB, Chen WZ, Zou JZ, Bai J, Zhu H, et al. Extracorporeal focused ultrasound surgery for treatment of human solid carcinomas: early Chinese clinical experience. Ultrasound Med Biol. Feb. 2004;30(2):245-60.
Xia R, Thittai AK. Real-time monitoring of high-intensity focused ultrasound treatment using axial strain and axial-shear strain elastograms. Ultrasound Med Biol. Mar. 2014;40(3):485-95.
Ye G, Smith PP, Noble JA. Model-based ultrasound temperature visualization during and following HIFU exposure. Ultrasound Med Biol. Feb. 2010;36(2):234-49.
Zhang SY, Zhou FY, Wan MX, Wei M, Fu QY, Wang X, et al. Feasibility of using Nakagami distribution in evaluating the formation of ultrasound-induced thermal lesions. J Acoust Soc Am. Jun. 2012;131(6):4836-44.
Zhao, Weiyuan, "Real-time Temperature Imaging Using Ultrasonic Change in Backscattered Energy" (2014). Engineering and Applied Science Theses & Dissertations. 17.
Zhou Z, Wu S, Wang CY, Ma HY, Lin CC, Tsui PH. Monitoring Radiofrequency Ablation Using Real-Time Ultrasound Nakagami Imaging Combined with Frequency and Temporal Compounding Techniques. PLOS ONE. Feb. 6, 2015.

* cited by examiner

$$CC_A(i,j) = \frac{\sum_i \sum_j ([S_0(i,j) - \overline{S_0}] * [S_1(i,j) - \overline{S_1}])}{\sqrt{\sum_i \sum_j (S_0(i,j) - \overline{S_0})^2 * \sum_i \sum_j (S_1(i,j) - \overline{S_1})^2}}$$

*Fig.6*

$$CC_A(i,j,k) = \frac{\sum_i \sum_j \sum_k ([S_0(i,j,k) - \overline{S_0}] * [S_1(i,j,k) - \overline{S_1}])}{\sqrt{\sum_i \sum_j \sum_k (S_0(i,j,k) - \overline{S_0})^2 * \sum_i \sum_j \sum_k (S_1(i,j,k) - \overline{S_1})^2}}$$

*Fig.7*

$$\Delta T = \frac{C_0}{2} * k * \frac{\partial(\Delta t(y))}{\partial y}$$

*Fig.8*

$$\beta = \frac{1}{C_0} * \frac{\partial(\Delta t(y))}{\partial T}$$

*Fig.9*

$$Y = \frac{\sum_{m=-M}^{M/2} \sum_{n=-N/2}^{N/2} (IQ^*_{ref}(m_0+m, n_0+n) \cdot IQ_{new}(m_0+m, n_0+n))}{\sqrt{\sum_{m=-M}^{M/2} \sum_{n=-N/2}^{N/2} |IQ^*_{ref}(m_0+m, n_0+n)|^2} \sqrt{\sum_{m=-M}^{M/2} \sum_{n=-N/2}^{N/2} |IQ_{new}(m_0+m, n_0+n)|^2}}$$

*Fig.10*

$$Y = \frac{\sum_{m=-K}^{K/2} \sum_{n=-L/2}^{L/2} (IQ_{new}(m_0+m, n_0+n) \cdot IQ^*_{ref}(m_0+m+i, n_0+n+j))}{\sqrt{\sum_{m=-L/2}^{K/2} \sum_{n=-K/2}^{L/2} |IQ_{new}(m_0+m, n_0+n)|^2} \sqrt{\sum_{m=-M}^{M/2} \sum_{n=-N/2}^{N/2} |IQ_{ref}(m_0+m+i, n_0+n+j)|^2}}$$

ULTRASOUND THERMOMETRY FOR ESOPHAGEAL OR OTHER TISSUE PROTECTION DURING ABLATION

CROSS-REFERENCE TO RELATED APPLICATIONS

This application claims benefit under Title 35, United States Code § 119(e) of U.S. Provisional Application No. 62/635,770 filed on Feb. 27, 2018, U.S. Provisional Application No. 62/723,366 filed on Aug. 27, 2018 and U.S. Provisional Application No. 62/735,571 filed on Sep. 24, 2018.

FIELD OF THE INVENTION

The following invention relates to methods for protecting sensitive bodily structures from thermal damage during ablation procedures upon a patient, such as cardiac ablation procedures. More particularly, this invention relates to use of ultrasound thermometry to monitor tissue temperature and protect against damage to sensitive tissues nearby where an ablation procedure is being conducted.

BACKGROUND OF THE INVENTION

Multiple thermal therapies have been used for treating diseases. Temperature monitoring has been used for monitoring damage to tissue both for assessing efficacy to the targeted tissue, and for protecting tissue for unwanted damage. Image guided thermometry using magnetic resonance is now seen in the clinical setting. However, compared with magnetic resonance, image guidance with ultrasound is portable, inexpensive, simple, and accessible.

Treatment of atrial fibrillation also involve ablative energies. These diverse energy sources such as radio-frequency, cryotherapy, microwave, laser and ultrasound can cause elevated or decreased temperature damage to the targeted tissue. Thermal esophageal injury is not uncommon, seen as ulcerations or nerve damage of the esophagus following an ablation, and can cause mortality, as in an atrial esophageal fistula.

Multiple strategies have been proposed and utilized to protect the esophagus, however, no strategy has been shown to consistently protect the esophagus during ablation. Intraluminal temperature monitoring of the esophagus has been widely used, however the protective value has been controversial. Cooling of the esophagus has been suggested, however despite ice solution being placed in the esophagus, esophageal ulcerations still developed following ablative therapy within the left atria. Manipulation of the esophagus with a transesophageal probe or by other means, away from the site of ablation has also not been consistently effective. Placing a balloon in the pericardial space between the esophagus and left atria has been proposed, but has the additional risk of a pericardiocentesis.

Mapping the esophagus with an EP mapping catheter to be displayed on an EP mapping system is frequently used, but only displays the lumen of the esophagus and not the interface of the outer esophagus and left atria. I have previously proposed intra-esophageal ultrasound or transesophageal ultrasound to delineate the outer perimeter of the esophagus relative to the left atria on an EP mapping system, as disclosed in co-pending U.S. patent application Ser. No. 16/282,835 filed on Feb. 22, 2019, incorporated herein by reference in its entirety.

Various commercially available cardiac electrophysiology mapping systems use different modalities to identify locality of catheters within the body. The St. Jude ENSITE system, a trademark of St. Jude Medical, Atrial Fibrillation Division, Inc. of St. Paul, Minn., uses impedance to localize various catheters relative to a stable catheter located within the heart. There is a background circuit utilizing a high frequency transthoracic electric field between the catheters and body surface electrodes, which detect impedance changes relative to a stable cardiac catheter (usually located within the coronary sinus) to derive location information within the heart. Consequently, this existing cardiac electrophysiology mapping system can utilize bipolar/unipolar electrode impedance and/or electrical current to determine the location of these electrodes in a three-dimensional space relative to a set of reference electrodes.

Another mapping system produced by Biosense Webster utilizes a magnetic field and a magnetic sensor to localize catheter location. A magnetic field is created around the thorax, and a magnetic sensor equipped catheter within this three-dimensional field is localized to a precision within 1 mm. These mapping systems can combine anatomical information from computer tomographic imaging, fluoroscopy and intravascular echo into the electrical mapping system. These include endocardial, epicardial and importantly pericardial structures, without the need of active fluoroscopy. One such EP mapping system is disclosed in U.S. Pat. No. 8,825,144, incorporated herein by reference in its entirety.

With this invention, I propose using an ultrasound probe which can be esophageal or transgastric in location, intracardiac, intravascular, or externally on the chest (transthoracic), to provide thermal imaging of the esophagus or other vulnerable tissue adjacent to the heart or other tissues such as the pulmonary veins, or other lung tissues. Ultrasound thermometry (a general term for ultrasound based thermal sensing) using various methodologies has attempted to monitor tissue being ablated with various energies (radiofrequency, cryoablation, ultrasound energy, microwave energy, laser etc.). However, ultrasound thermometry has been limited by difficulties in accurately measuring temperature above 45° C. and below 0° C. In addition, many methodologies of ultrasound thermometry are extremely motion sensitive making this technique difficult to apply in a biological setting.

Three-dimensional mapping systems such as the cardiac electrophysiology mapping systems identified above, are used to localize ablation applications in a three-dimensional space. For example, cardiac electrophysiology mapping systems traditionally use a magnetic field or electric field (using electrical impedance or electrical current) to provide locational information within the heart.

Ultrasound transducers for three-dimensional mapping systems such as cardiac electrophysiology mapping systems have traditionally incorporated two-dimensional images, to construct a three-dimensional construct, such as with intracardiac ultrasound incorporated into the EP mapping system. Other standard and three-dimensional ultrasound systems and mapping systems have not used ultrasound thermometry because of the inherent limitations of signal to noise ratio, temperature measurement in non-ablative ranges, and motion.

SUMMARY OF THE INVENTION

Ultrasound thermometry takes advantage of the relatively predictable change in the speed of sound with temperature change in various materials and/or change in back scattered energy, which is based on heat induced change in backscatter coefficient. Ultrasound thermometry during ablation of cancer has been extensively studied in the oncology literature, but has had difficulties measuring high temperatures. For most tissues, the speed of sound increases with temperatures up to 60° C. However, the speed of sound correlates poorly with high temperatures (greater than 45°-50° C.), making temperature measurements difficult at the ablative temperatures. Ultrasound thermometry has been feasible and relatively accurate in hyperthermic temperatures (less than 45°-50° C.) especially mild hyperthermia (less than 41° C.). Since change in temperature using various methods of ultrasound thermometry tends to have a linear relationship below temperatures of 45°-50° C., this invention measures temperature in vulnerable tissue adjacent to the ablation zone.

For example, ablation for atrial fibrillation frequently entails using ablative energy such as radio-frequency, laser, or cryotherapy on the posterior wall of the left atria. The esophagus is adjacent to this area and serious consequences from esophageal injury can result. An ultrasound probe within the esophagus during ablation of the posterior wall of the left atria is used (as one option) to measure temperature on the myocardium, pericardium, epicardium or outer diameter of the esophagus directly opposite the cardiac tissue being ablated. Hyperthermia or hypothermia in tissue that needs to be protected is detected by ultrasound thermometry, and the ablative energy can be modulated or discontinued. Temperature at the tissue being ablated can also be measured, (although it may be limited by the nonlinear and less predictable ultrasound characteristics at higher temperatures, but may be useful in lower temperatures for cryotherapy).

Various ultrasound acquisition geometries could be utilized such as passive acoustic mapping, pulse echo (most common in the medical field), pitch catch or hybrid geometries. Passive acoustic imaging is derived from cavitation and thermal strain of tissues. Pulse echo uses a transducer that both transmits and receives acoustic waves that interact with the tissue. With pitch catch, the transmitting and receiving transducers are offset from each other. For example, the transmitting and receiving transducers can face each other. Another pitch catch possibility is where transmitted acoustic waves are captured at many different angles, so called full aperture tomographic geometry. Hybrid geometries can combine ultrasound thermometry with other imaging modalities into a system to enhance temperature acquisition and resolution. Ultrasound acquisition geometries that are being developed or not yet conceived, could also be utilized.

Multiple methodologies for ultrasound thermometry could be used to measure change in temperature, including B mode imaging, Nakagami Imaging, speckle tracking and thermal strain imaging, passive monitoring, back scattered imaging and quantitative ultrasound, tissue stiffness and elastography including shear wave thermometry, local harmonic motion imaging, stimulated acoustic emissions, mean scatter resonance, and photo acoustic imaging. Other methodologies that could be used include phase contrast and thermoacoustic lensing, ultrasound tomography, and hybrids of one or more modalities. Many of these methods can use already FDA approved probes. Other methodologies could also be used, but at the time of this writing are research methods, requiring customized transducers, lasers or mechanical stimulators.

A combination of methodologies or methodologies known, being developed, and not yet conceived for ultrasound thermometry could also be employed to increase accuracy and range of temperature measurements available.

This invention is described in most detail with regard to speckle tracking imaging. Specifically exploring echo time shift method and cross-correlation speckle tracking for ultrasound thermography using pulse echo, although other ultrasound thermographic methodologies could also be utilized.

Beneficially, the methods of this invention are integrated with a three-dimensional mapping system such as a cardiac electrophysiology (EP) mapping system, to delineate ablation points that achieve a certain temperature and to correct for motion in the ultrasound measurement of temperature. In addition, a three-dimensional ultrasound transducer, coupled with a magnetic sensor for a three-dimensional mapping system, is used for ultrasound thermometry and to define nearby anatomy.

Ablated tissue could be delineated within tissue once a certain temperature is achieved at that point in a three-dimensional mapping system for any tissue. For example, in currently commercially available cardiac electrophysiology mapping systems (Biosense Webster and St. Jude), temperature is measured at the tissue-catheter electrode interface (usually at the endocardium) while ablation is occurring. Temperature within the myocardium could be measured using ultrasound thermometry. However, ultrasound thermometry has difficulties measuring temperature above 45° C. and below 0° C. Once a certain temperature is achieved for a given amount of time, and a certain amount of density in the ultrasound window, this location could be transposed onto a three-dimensional mapping system such as a cardiac electrophysiology mapping system. In this example, a cardiac electrophysiology mapping system could mark a point within a three-dimensional space once a certain threshold temperature is achieved for a certain amount of time. Thus, an estimation of the depth and width of the volume affected by ablation energy can be visualized on the cardiac electrophysiology mapping system. This principle could be applied broadly to other mapping systems for other tissues, to treat other disease processes such as cancer.

In one embodiment of the invention, before an ablation procedure is conducted, an ultrasound probe is located so that a target area associated with the ultrasound probe includes tissues to be protected from thermal damage during the ablation procedure. As an example, if the ablation is a coronary ablation procedure, such as within the left atrium of the heart, the ultrasound probe could be a transesophageal echo probe placed within the esophagus at a location closest to the heart. A piezo source on the echo probe would be oriented generally facing toward the heart. The echo probe would be activated before any thermal energy has been applied to the heart and a baseline image would be obtained which includes within the target area of this image, structures to be protected from thermal damage. The structures could include the wall of the esophagus, and especially the outer wall of the esophagus, as well as the epicardium, and other nearby structures, including pulmonary tissues.

This initial image acquired by the echo probe, in one embodiment, is integrated into an EP mapping system which has already been put into operation, and which preferably is also coordinated with an ablation catheter to be used during the ablation procedure. The initial images obtained from the echo probe act as a baseline. In fact, as many as each pixel within the image obtained by the echo probe could provide a separate baseline (or a portion of a multi-pixel baseline) for an associated tissue structure. These tissue structures are imaged by bouncing ultrasonic sound waves off of the tissues, and then detecting the reflected sound waves at a sensor which is typically also on the echo probe. As an enhancement to this baseline, various different modalities of tissue motion can be briefly studied, such as peristalsis motion, motion associated with movement of the echo probe itself, motion associated with beating of the heart, motion associated with respiration of the patient, and motion from other motion inducing origins.

When the baseline information associated with the ultrasound image has been appropriately gathered and stored as a baseline for the image, the ablation procedure can proceed. Especially if the ablation location is also within the image produced by the echo probe, the rapid change in temperature at the ablation site will result in a change in the speed of sound associated with passage of ultrasound waves through these heated tissues, and involving faster propagation of sound through the tissues with increasing temperature. The image is processed and distortions to the image resulting from the change in speed of sound are detected and correlated with a corresponding amount of temperature change. This temperature change can be outputted in a variety of ways. In one embodiment, this temperature change is depicted on a visual presentation of the echo probe generated image, such as in the form of a different color for the image matching the temperature involved (e.g. black or dark red) for the highest increase in temperature, red for the next highest increase, orange for the next highest increase, green for the next highest increase (or to represent a least amount of temperature decrease), blue for a greater amount of temperature decrease, and purple for a greatest amount of temperature decrease. As another alternative, numerical values for temperature could be placed adjacent to the tissues undergoing temperature change. According to various methodologies, including those disclosed herein, motion such as that produced by one of the modalities and origins identified above is accounted for, so that such motion is not improperly interpreted as temperature change.

A medical professional performing an ablation procedure or assisting with the ablation procedure can monitor such a coded echo probe image including temperature information associated with various different tissues of interest. As ablation energy causes temperature increase (or decrease) at the ablation site, such temperature changes propagate through various different modes of heat transfer to adjacent tissues. The corresponding changes in temperature of these tissues can be monitored. If any tissues which are sensitive to temperature change encounter undesirably high temperature changes, or are approaching undesirable thresholds, an ablation procedure can be stopped or paused, or can be adjusted, such as by utilizing lower energy levels, or by moving a tip of the ablation catheter to other areas for further conducting of the ablation procedure. As a result, a highly effective ablation procedure can be performed with minimization of thermal damage to sensitive tissues adjacent thereto.

According to one aspect of this invention, this invention is directed to a method for ablation of bodily structures while protecting adjacent tissues from damage, the method including the steps of placing an ablation tool adjacent to a target bodily structure to be ablated, locating an ultrasound probe within range of tissues to be protected; operating the ablation tool to ablate the target bodily structure, evaluating ultrasound probe data during said operating step to determine temperature changes of tissues to be protected, based at least partially on detection of changes in speed of sound within the tissues to be protected, the speed change associated with temperature change, and adjusting said operating step when said evaluating step detects undesirable temperature change in the tissues to be protected. The operating step of this method can include discharge of electric arc energy from the ablation tool. The operating step can alternatively include discharge of laser energy from the ablation tool. The operating step can alternatively include discharge of radio-frequency energy from the ablation tool. The operating step can alternatively include the discharge of ultrasonic energy from the ablation tool. The operating step can alternatively include cryogenic transfer of heat from the target bodily structure to the ablation tool to oblate by cooling in the target bodily structure.

The evaluating step of the above method can include displaying an image of tissues to be protected along with a visual indication of temperature of the tissues. This temperature visualization can include different colors indicative of different temperatures with the colors displayed upon the depiction of tissues to be protected. The temperature visualization of the evaluating step can be overlaid upon a display of an EP mapping system which is also displaying tissues to be protected.

The adjusting step of the above method can include the user pausing the operating step. The adjusting step can alternatively or in addition involve the user moving the ablation tool away from tissues to be protected. The adjusting step can include decreasing a power level of the ablation tool. Such decreasing of power can occur automatically when a threshold temperature is detected in tissues to be protected, such as according to a feedback loop which has as an input temperature of tissue to be protected and as an output a gain value controlling power to the ablation tool. The decreasing step can be terminated when temperature change of tissues to be protected drops below a desired maximum level (or above a minimum level for cryo ablation) of temperature change, so that full power ablation can re-commence.

Target body structures for protection according to the above method of this invention can include a portion of the patient's myocardium, epicardium, pericardium, pulmonary tissues, esophagus or other tissues. Such esophageal tissues to be protected can include an outer wall of the esophagus and/or an inner wall of the esophagus or surrounding associated tissues. The locating step of the method described above can involve locating the ultrasound probe within the esophagus or at other locations including intracardiac locations, subcutaneous locations or supracutaneous locations.

The evaluating step of the above identified method, in at least some embodiments includes correction for relative motion. Such relative motion can include relative motion between the ultrasound probe and bodily structures, or can include motion between different bodily structures, or can include motion between bodily structures and an EP mapping system and/or motion between the ultrasound probe and the EP mapping system. If multiple different ultrasound probe sources and ultrasound wave sensors are separately provided, such motion correction could correct for motion between such ultrasound sources and ultrasound sensors.

OBJECTS OF THE INVENTION

Accordingly, a primary object of the present invention is to utilize ultrasound thermometry for soft tissue being ablated and adjacent soft tissue, such as tissue to be protected from thermal damage.

Another object of the present invention is to utilize ultrasound thermometry in conjunction with a three-dimensional mapping system for ablation delineation and tissue protection.

Another object of the present invention is to utilize ultrasound thermometry in conjunction with a three-dimensional mapping system for ablation delineation and tissue protection and with motion correction.

Another object of the present invention is to measure temperature by ultrasound thermography adjacent to tissue being ablated to limit bystander tissue damage such as the esophagus.

Another object of the present invention is to measure temperature by ultrasound thermography of tissue being ablated and adjacent tissue to delimit target zone, such as the myocardium.

Another object of the present invention is to measure temperature of tissue being ablated by ultrasound thermography with point marking in a three-dimensional mapping system such as a cardiac electrophysiology mapping system, once a threshold temperature is achieved.

Another object of the present invention is to utilize motion correction for ultrasound thermometry for ablation delineation and adjacent tissue protection, such as the esophagus, utilizing a three-dimensional mapping system such as a cardiac electrophysiology mapping system.

Another object of the present invention is to provide a design for an ultrasound transducer to allow for three-dimensional acquisition or improved two-dimensional acquisition in a three-dimensional mapping system, such as a cardiac electrophysiology mapping system.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to an ultrasound thermometry system especially for use with an electrophysiology (EP) mapping system 45. Such a thermometry system 10 can be useful to protect thermally sensitive tissues adjacent to a heat source, such as an ablation catheter, by monitoring temperature at various areas.

Figure 1:
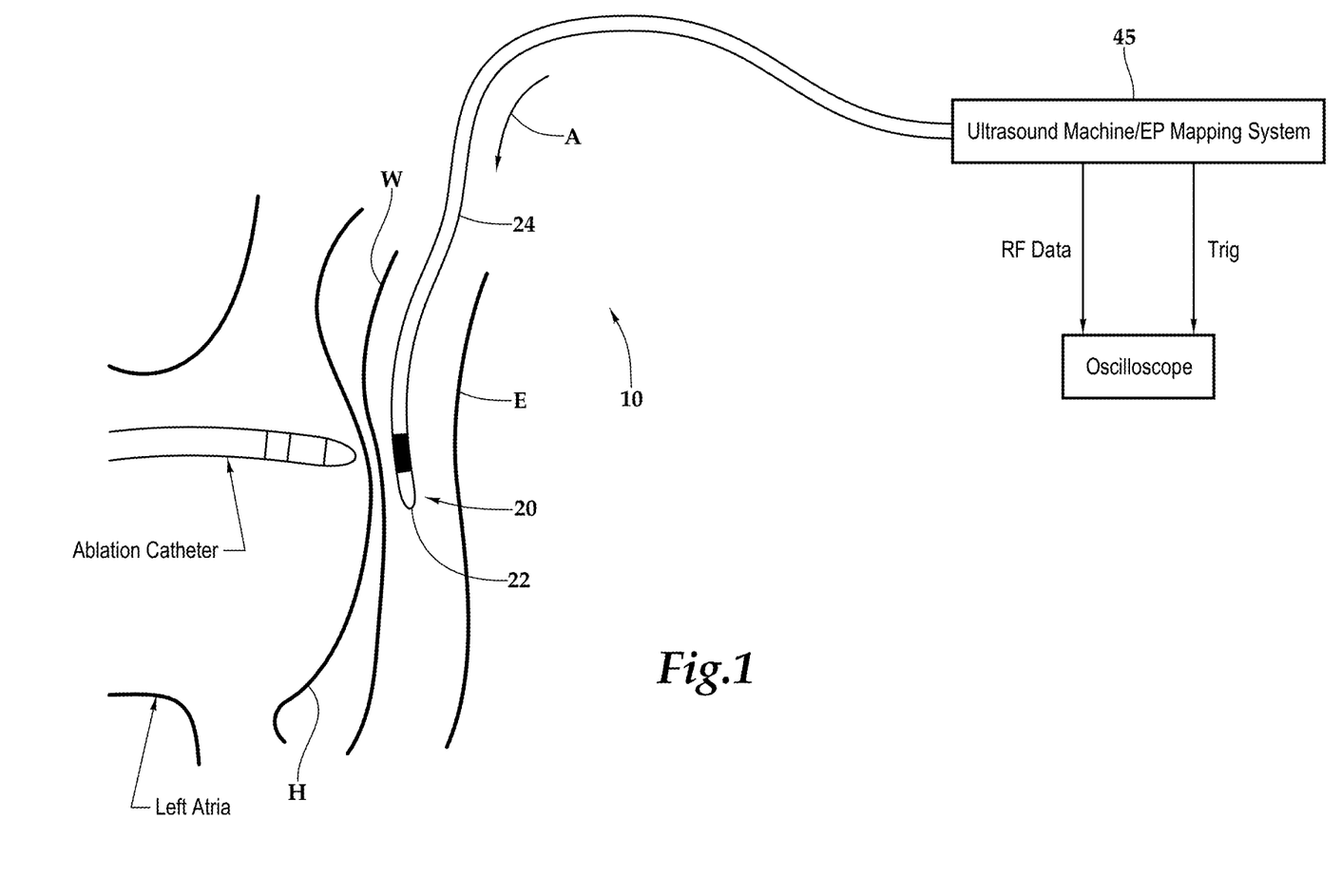
FIG. 1 is a schematic of a chest cavity of a patient and adjacent equipment, illustrating placement of an ablation catheter and an ultrasound probe for ultrasound thermometry and tissue protection adjacent to an ablation site within a patient's heart, according to a method of this invention.
Figures 12, 13:
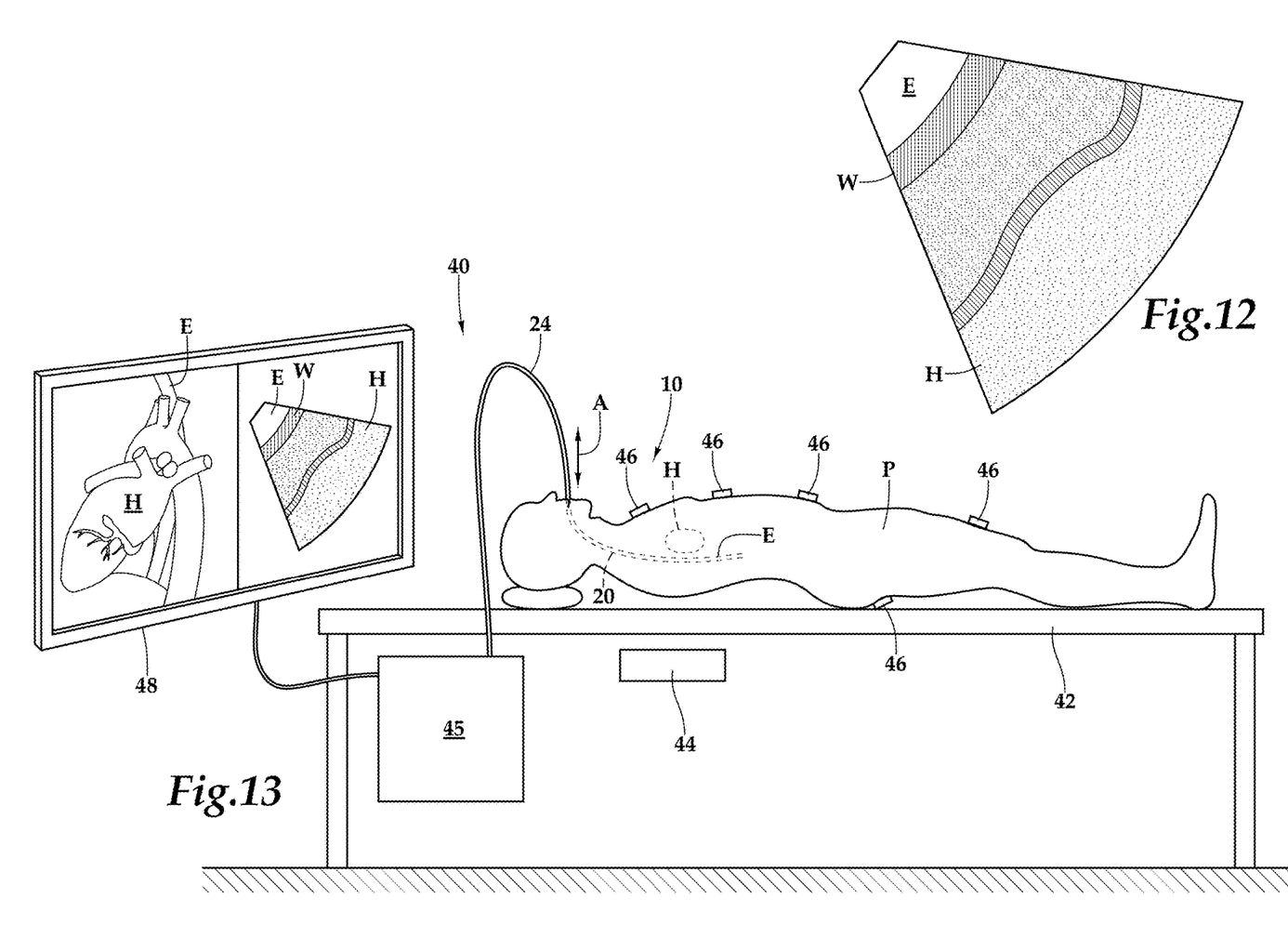
FIG. 12 is a schematic depiction of an ultrasound window produced by an ultrasound probe within an esophagus of a patient, near a heart of a patient, and providing an image which could then be color labeled or numerically labeled, or otherwise labeled to overlay temperature data gathered according to this invention upon such an image for monitoring by a surgeon or other medical professionals during a cardiac ablation procedure within the heart or during some other thermal procedure.
FIG. 13 is a front elevation view of a patient upon a table within an electrophysiology surgical procedure suite which includes an EP mapping system and which illustrates how an esophageal echo probe can be placed within the patient's esophagus and near the heart, for conducting ultrasound thermometry and for tissue protection during an ablation procedure. A display as part of the EP mapping system generally depicts how standard EP mapping data can be imaged, such as for guiding of the ablation procedure, while a separate portion of the same display (or a second display) provides ultrasound imaging data along with ultrasound thermometry data to further guide medical professionals in safely conducting ablation procedures without thermal damage to adjacent tissues, such as the wall of the esophagus.
Figure 14:
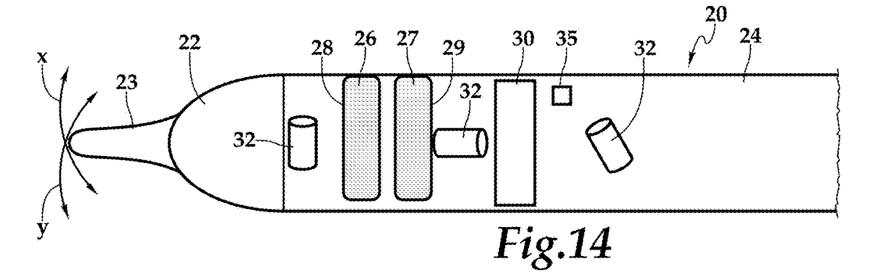
FIGS. 14-18 are plan views of a schematic nature of distal ends of intraluminal ultrasound probes, such as transesophageal echo probes, for providing ultrasound signals which are amenable to processing for generation of ultrasound thermometry data.
Figure 15:
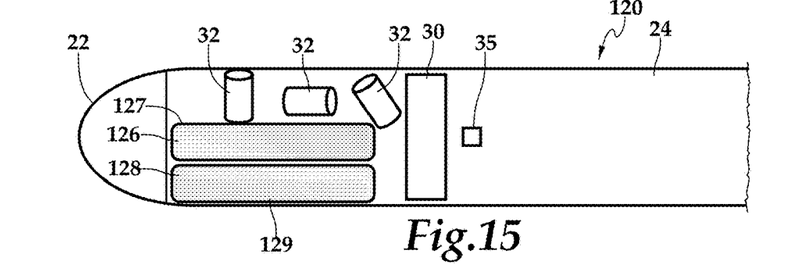

In essence, and with particular reference to FIGS. 1 and 13, the system 10 is described according to a typical embodiment. The system 10 can be implemented with an ultrasound probe 20 located near tissues to protect. For instance, the probe 20 can be placed in the esophagus E to protect the wall W of the esophagus. The ultrasound thermometry system 10 can be used in an EP mapping suite 40 along with the EP mapping system 45 to add the benefits of thermometry to procedures performed in the suite 40, such as cardiac ablation procedures. The thermometry system incorporates motion compensation to enhance accuracy of thermal strain and/or temperature related outputs.

Figure 3:
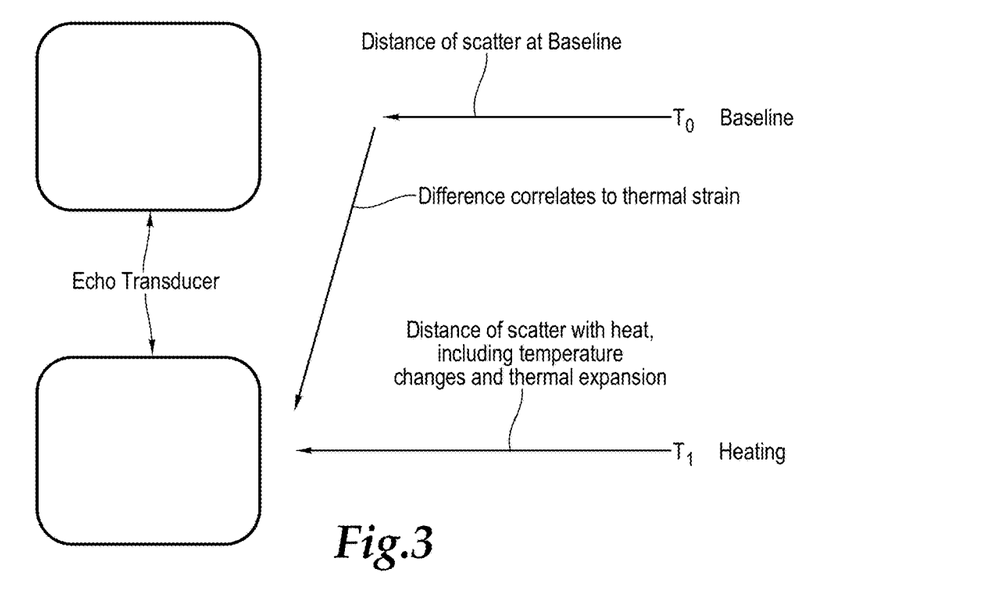
FIG. 3 is a schematic depicting how differences in magnitude of sound wave vectors between a baseline condition and when heating is occurring, can be measured and correlated with temperature change.

More specifically, and with reference to FIG. 3, a schematic depiction is provided of baseline time of scatter from a specific depth. A bottom portion of FIG. 3 similarly depicts time of scatter with temperature change, and how scatter shifts to a different location with new time of arrival. The time of scatter with heating includes time of scatter, linear coefficient of thermal expansion $(1-\alpha_t)$, and temperature changes. The difference can be calculated as time shift (diagonal arrow) which different correlates with temperature change, at least partially. Thermal expansion and temperature generally have opposing effects on the speed of sound. However, the change is speed of sound with temperature change generally dominates thermal expansion by an order of magnitude.

Figure 4:
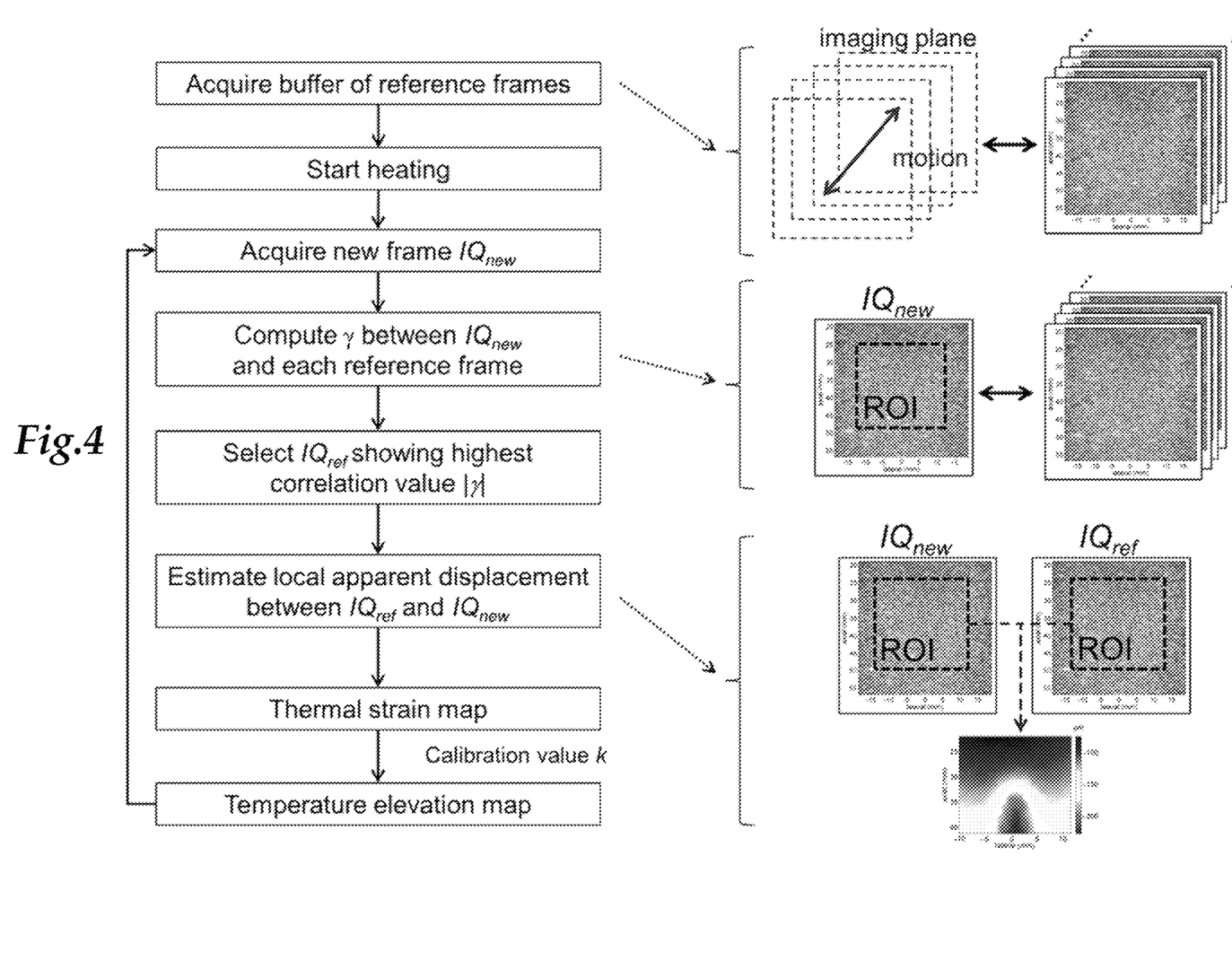
FIG. 4 is a flow chart with associated example images illustrating how ultrasound image frames can be used to create a motion compensated temperature elevation map indicating temperature of tissues being imaged.
Figure 5:
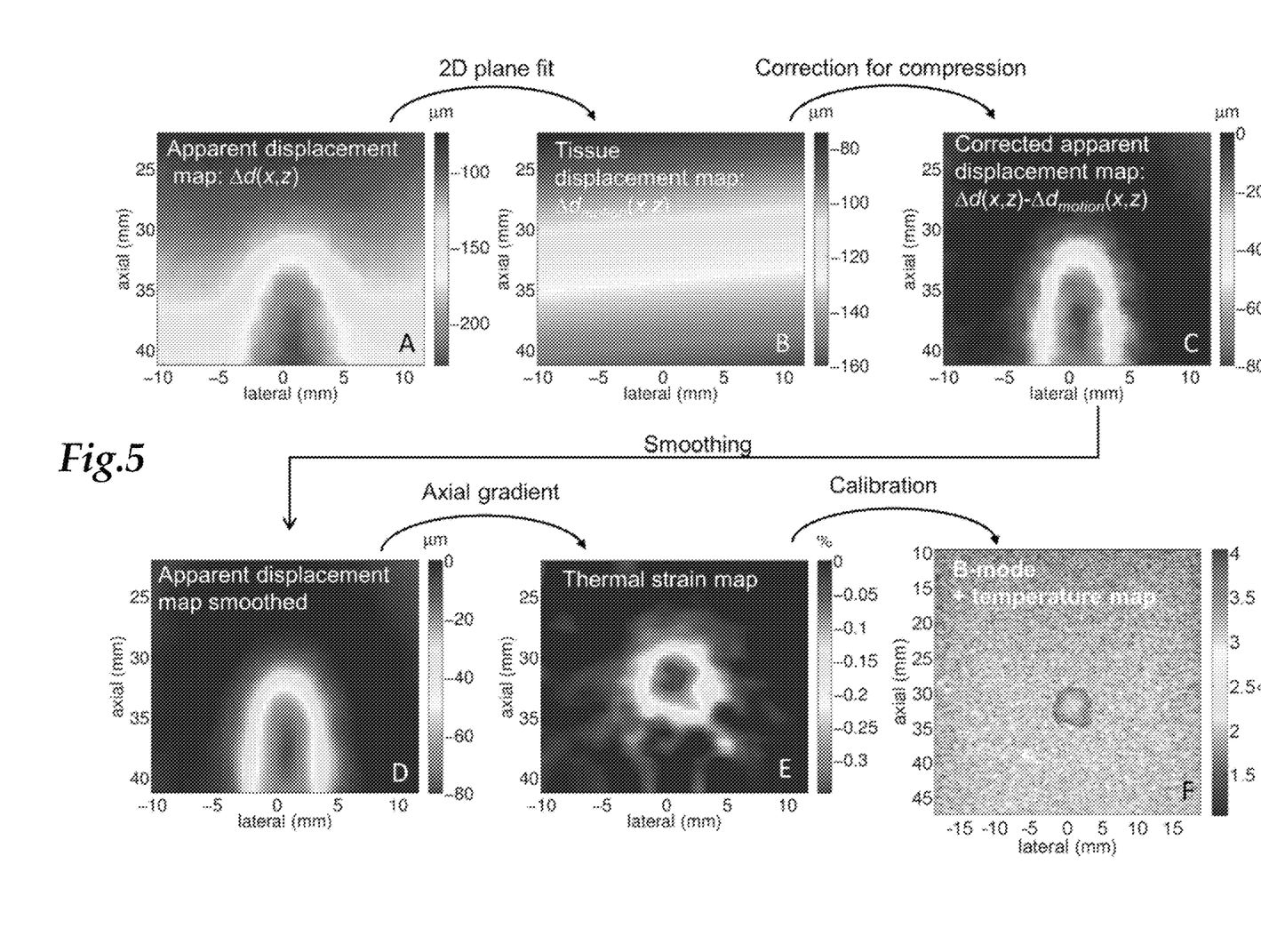
FIG. 5 depicts a progression of images and image processing steps according to this invention which further illustrate compensation for motion when creating a temperature elevation map.

Most ultrasound thermometry measurements are extremely sensitive to motion which is inherent to biological systems which (without compensation) severely decreases the applicability of this technology. Any ultrasound thermometry methodology could be used for motion correction. For instance, multiple reference frames can be used in a buffer (also called a baseline buffer or baseline data) prior to heating, to be compared with new frames as the tissue is being heated, which can be matched and compared for thermal strain calculations. This methodology is akin to that proposed by Foiret and Ferrara (FIGS. 4 and 5).

An additional enhancement for motion correction includes the ability of the operator to specify an area within the region of interest which was going to potentially be heated based on the location of the heating source (in one example, the ablation catheter within the left atria). For example, a cardiac electrophysiology (EP) mapping system, or the ultrasound transducer within the esophagus can be used to give the catheter location and the operator can provide the most likely area within the esophagus to get heated, where thermal strain maps (or other thermal readings) can be generated. While the other areas of the region of interest in the heated frames could be used for matching purposes with buffered reference frames. The process of identifying the most likely location to be heated or cooled with the region of interest could also be automated, based on the location of the catheter relative to the esophagus E.

An alternative motion correction utilizes locational data from a three-dimensional mapping system such as the cardiac electrophysiology (EP) mapping system 45. The x, y, z coordinates of the ultrasound catheter and the directional information within the cardiac electrophysiology (EP) mapping system 45 could be used to mark different reference frames at different locations and be used to match for comparison with new frames as tissue is being ablated (hyperthermia or hypothermia).

In addition, or alternatively, one or more points within the ultrasound system 10 imaging output window or region of interest from the ultrasound transducer with magnetic sensors and/or electrodes could be used to mark locational information relative to the magnetic sensor. Reference frames can be compared with new frames as tissue is being heated for calculating thermal strain (or other temperature information) using these points within the ultrasound system 10 image output window.

The above methodologies using a three-dimensional mapping system for motion correction can also be used in conjunction with having a buffer of reference frames at baseline and matching to new frames during heating. Using a combination of buffered images and locational points within a three-dimensional mapping system may be advantageous since tissue movement may occur despite similar location and orientation of the transducer within the three-dimensional mapping system.

A possible interface between these two motion correction algorithms could be the following: different ranges of locations within the three-dimensional mapping system for the ultrasound probe 20 transducer and/or the ultrasound window with a region of interest could have separate bins. Each bin can have a collection of images which provide reference values of thermal strain for cross correlation. As the tissue is heated, the new location of the transducer and/or ultrasound window can be used, and compared with the appropriate matching bin, and that set of images which most closely matches the cross correlational value can be used for reference frames to estimate thermal strain.

An alert can also be provided for the operator when the transducer has moved from the original location where reference frames were obtained. If there is a significant change in the x, y, z coordinate in the three-dimensional mapping system, then the system warns the operator that a new set of reference frames need to be obtained.

Another possible interface could include incorporating the x, y, z coordinate measurements from the three-dimensional mapping system into the calculations for ultrasound thermometry. For example, a correction factor using none, some or all of the x, y, z coordinates can be placed into the thermal strain calculations. For example standard thermal strain can use cross correlation at a point i, j, following the equation depicted in FIG. 6.

Figure 6:
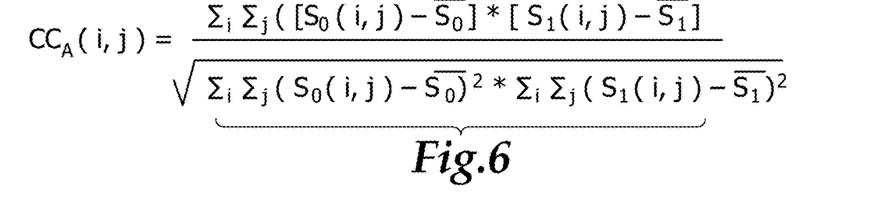
FIGS. 6-11 depict exemplary formulas utilized in one embodiment of this invention for utilizing ultrasound signals for measuring temperature change according to forms of this invention.
Figure 7:
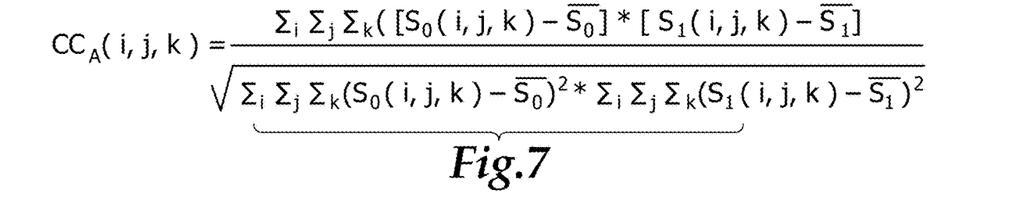

The cross correlation calculation can include a third dimensional component to take into account multiple rows of piezoelectric crystals and/or using coordinates from a three dimensional mapping system, such as a cardiac electrophysiology (EP) mapping system 45, following the equation of FIG. 7. In the equations of FIGS. 6 and 7, $S_0$ and $S_1$ are baselines, and subsequent data and bar quantities are spatial averages. Three-dimensional coordinates, as outlined above can include i, j, k and be use in cross-correlation analysis of thermal strain since the ultrasound transducer can have multiple rows (for the k axis). A correction factor which can be derived from the cardiac electrophysiology (EP) mapping system 45 could be used to modify the coordinates outlined above (i, j, k) to correct for motion of the transducer.

Methods to account for tissue movement are preferably used. For example, the esophagus E can have a contracted state, relaxed state, or transition state. Each state could have a bin for different thermal strain values which could be buffered at baseline and be compared to corresponding values during application of energy. Another method to account for tissue movement is to track certain tissue, for example, the outer diameter of the esophagus E. Thermal strain within the esophagus E can be calculated when the outer diameter of the wall W esophagus E is at different depths, relative to the ultrasound transducer. When the tissue is heated, matching reference frames for the outer diameter of the esophagus E can be compared with frames as tissue is undergoing temperature change.

Figure 2:
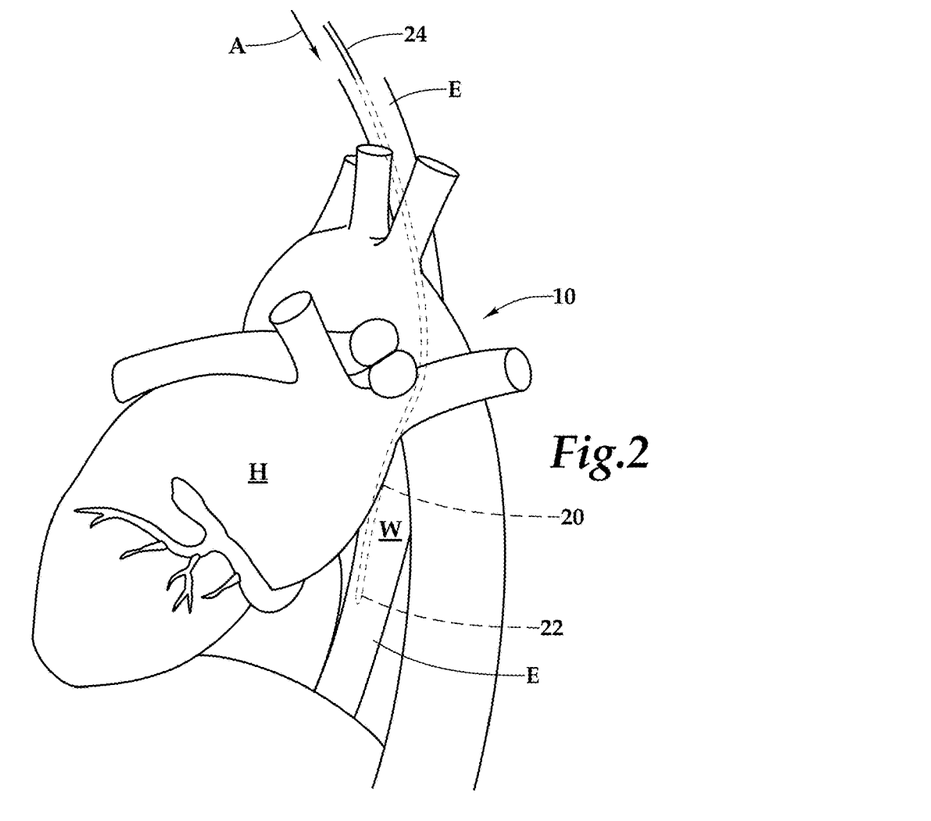
FIG. 2 is a schematic of a human heart and adjacent bodily structures, and further illustrating one position for an ultrasound probe when primarily protecting esophagus tissues from thermal damage during a cardiac ablation procedure.

Tissue movement from respiration can cause variations in the location of various organs, which provides barriers for ultrasound thermometry. An example within the chest cavity includes the heart H and the esophagus E (FIGS. 1, 2 and 13) relative to a transducer at any location. Cardiac electrophysiology (EP) mapping systems 45 can gate respiration, and usually map points are taken during the end expiratory phase. Similarly, ultrasound probe 20 data acquisition can be linked with the respiratory phase as gated by the cardiac electrophysiology (EP) mapping system 45. Thus, reference frames and measurements can be compared with heated time frames during comparable points of respiration, so that different bins of frames for comparison can be used during different cycles of respiration. This process could be automated or manually driven.

Figure 8:
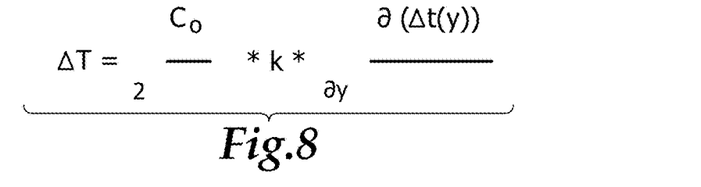
Figure 9:
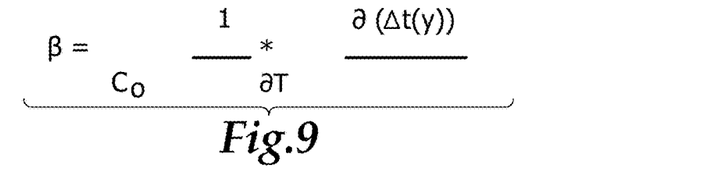
Figure 10:
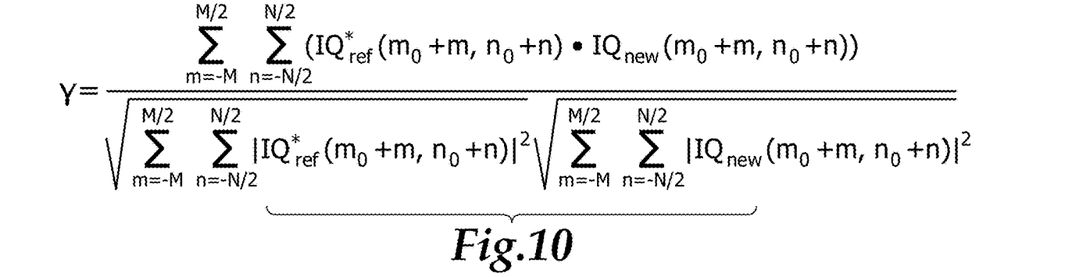

With no motion during imaging (low motion areas such as the pericardium or outer esophagus E diameter), the displacement of ultrasound speckle from local heating is associated with changes in the speed of sound in the tissue and thermal expansion of the tissue. Thermal expansion and temperature change can be estimated by time shift from echo data ($\Delta t$). Where the speed of sound is $c_o$ at baseline temperature $T_o$, the change in temperature ($\Delta T$) at depth y, can be related to the changes in time shift at depth y, following the equation of FIG. 8, where $k=1/(\alpha_t-\beta)$ (which needs to be calibrated since this is material dependent). $\alpha_t$ is the thermal expansion coefficient and can be a function of temperature. Since $\alpha_t$ is relatively small in relation to the speed of sound and the change in $\alpha_t$ is relatively small in the hyperthermic temperature ranges, $\alpha_t$ may be constant, and, following the equation of FIG. 9, $\beta$ can be determined. For most biologic materials with temperature 20°-40° C., a linear relationship can be assumed for the speed of sound and temperature.

Most preferably, k values can automatically change with different temperatures. Values for k could also change based on tissue contracted state if necessary. Tissue movement such as respiration, cardiac motion, a peristalsis from the esophagus E could be gated as proposed.

Small temperature changes in the ambient body temperature range (37.8° C.) can be detected in adjacent tissue for purposes of tissue protection, despite the current limitations of ultrasound thermometry. An example would be protection of the esophagus E during ablation for atrial fibrillation within the left atria of the heart H (FIG. 1). The ultrasound system 10 could be interfaced with an EP mapping system 45, EP monitoring system, ablation energy generator (radio-frequency and cryotherapy as examples), or a standard ultrasound visualization machine or other system. The ablation zone tends to be greater than 2 mm, and would be in the temperature ranges where a linear relationship between cross-correlation speckle tracking for ultrasound thermography and actual temperature (measured as infrared in experimental models). Whether the temperature change was increasing (eg. radio-frequency ablation, laser ablation, ultrasound ablation), or decreasing (cryotherapy), small changes in adjacent soft tissue can be detected. Specific region(s) of interest can be imaged for temperature changes.

Information from displacements from gross patient motion can be used for motion correction or compensation with several temperature estimation methods. For example, Foiret and Ferrara proposed motion compensation by acquisition of multiple reference frames prior to treatment (see FIGS. 4 and 5). Two-dimensional cross correlation was used, using In-phase/Quadrature (IQ) beam formed data, where $IQ_{new}$ is the most recently acquired frame, $IQ_{ref}$ is the reference frame, M and N are the number of frames in the region of interest, in the axial and lateral dimensions, $m_0$ and $n_0$ are the indices at the center of the region of interest, and * is a complex conjugation.

Figure 11:
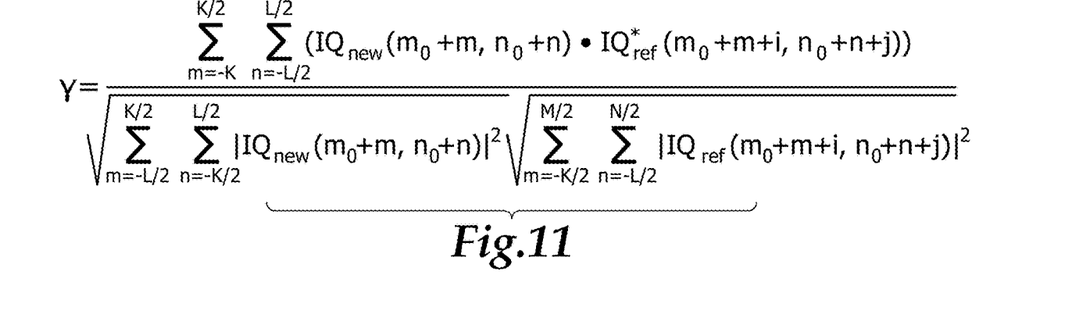

The complex cross-correlation between the reference frame and the current frame was expressed as following the formula of FIG. 11, where m and n are pixel position in the region of interest (kernel), i and j is the position of the kernel in the search area, K and L are the number of samples in the kernel in the axial and lateral dimensions and $m_0$ and $n_0$ are at the center of the kernel. Axial lag estimates from tissue motion is subtracted from the shift map, leaving displacement of scatterer from temperature change. The corrected map can be smoothed, axial gradient calculated to obtain a strain map and superimposed on the B mode image. Quantitative temperature measurements (e.g. temperature numbers on tissues having the number displayed thereon, or by use of color) could also be displayed possibly on the B mode image or cardiac electrophysiology (EP) mapping system 45 and the display 48 thereof. The display 48 can also show typical two-dimensional or three-dimensional images of interest gathered by the primary magnet 44 and/or other electrodes/sensors 46 placed upon a patient P resting upon a table 42 in an EP mapping suite 40 (FIG. 13).

Thermometry measurements could be gated with various movements. In the case of the esophagus E, based on peristalsis, and respiration. Peristalsis could be based on esophageal manometry measurements (such as intraluminal pressure of the esophagus E), or cyclical thickening and dilation of the esophagus E. For respiration, comparison of images/RF data can be specified during comparable portions of the respiratory cycle. For instance, comparable data at specific cycles of respiration can be analyzed. In the case of cardiac thermometry, beat to beat variation and respirations could be gated. In addition, different filters can be used for temperature estimation. Various filters described in the literature include median filters to mask erroneous large or small displacements and smoothen the lateral displacement gradient, gaussian filter, averaging filter, 1-D Savitzky-Golay filter.

If possible, myocardial temperature during ablation could also be measured, although ultrasound temperature has a nonlinear relationship with "true temperature" at temperatures greater than 50° C. Adaptive ultrasound imaging has been proposed to increase accuracy at higher temperatures such as during ablation. For example, in temperature estimation using time shift data, k, which is usually constant, such a modified system could use an adaptive k algorithm at certain temperature ranges which could be automatically applied. Methodologies that incorporate cardiac movement and respiration could also be utilized for myocardial temperature measurement as it is being ablated.

Ultrasound thermometry can, according to embodiments of this invention, also be used for temperature and lesion assessment of the myocardium during cryoablation. With particular reference to FIG. 1, one configuration for implantation of this invention is described according to one embodiment. An echo transducer (or other ultrasound probe 20) is placed in the esophagus E (along arrow A), facing the posterior aspect of the left atria of the heart H, and the ablation catheter. The ultrasound system 10 can be interfaced with an EP mapping system 45 and used within an EP mapping suite 40, and RF data from the probe 20 is sent to the oscilloscope. In turn, this data can be processed by a commercially available program such as Matlab or other ultrasound data processor or method. A processor or multiple processors could be designed to automatically and efficiently run calculations for commercial use. The ultrasound system 10 could also be interfaced with an EP monitoring system or ablation generator (for example radio-frequency or cryotherapy).

Other methodologies of ultrasound thermometry have similar limitations, but could be used with the similar rationale as previously outlined (ie. change of temperatures near body temperature). Multiple methodologies could also be utilized to increase accuracy and temperature range. For example, elastography could be used in combination with cavitation methodologies.

Temperature measurement is used to measure efficacy of ablative tissue, and to protect adjacent tissue from damage. Temperature can be measured by thermocouples, thermistors, resistant temperature detector, infrared, CT, and magnetic resonance. Many of these temperature measurement methods are invasive, ionizing, expensive and bulky. Ultrasound temperature measurement can be noninvasive to the tissue, non-ionizing, economical, and portable.

Temperature measurement requires temporal, spatial and temperature resolution. A temporal resolution within a few seconds, spatial resolution within a few millimeters, and temperature resolution less than 1° C. is required for ablation. Ideally ultrasound thermometry should provide rapid, accurate and precise temperature measurement between 0° to 100° C. Ultrasound thermometry using various methodologies have a relatively linear and accurate measurement between 20°-45° C. However above 50° C., there are multiple physical and acoustic barriers with ultrasound thermometry, including non-linear temperature dependence on contrast parameters, stochastic bubbles, and phase transitions.

Given these limitations, ultrasound thermometry can still be effective at measuring hyperthermia, and possibly temperature/lesion assessment for ablation. The current state of ultrasound thermometry can provide protection to the esophagus E, lungs and possibly lesion assessment in the myocardium. Surveillance of temperature can occur on the outer circumference of the esophagus, bronchus, pericardium and myocardium as ablation (radio-frequency, laser energy, cryoablation, etc.) within the left atria is being applied. Ultrasound thermometry in the literature have primarily been in the depths between 2-12 mm. The esophagus wall thickness W is about 4-6 mm in thickness, and places the outer circumference of the esophagus E well within the range of different ultrasound thermometry methodologies.

Ultrasound thermometry between 20°-45° C. can offer spatial resolution (2-4 mm), temperature resolution (less than 1° C.), and temporal resolution (speed of sound and processing speed). Hyperthermia can be measured on the outer circumference of the esophagus E, rather than the currently utilized intraluminal thermocouple/thermistor which may be a late signal for esophageal injury. For ablation involving cold temperatures, ablative lesion assessment within the myocardium may be an added bonus.

The speed of sound in various mediums could be measured, such as myocardium, pericardium and esophagus E, and applied to different ultrasound thermometry methodologies. In vitro studies on muscle tissue and cardiac mimicking tissue has been studied using depths comparable to esophageal thickness. These ultrasound methodologies could be tested in vivo in animal models using thermocouples or infrared at the esophagus E or pericardium. Human patients could be tested using magnetic resonance imaging as a gold standard, and examining for esophageal ulcerations or nerve plexus damage following usage of ultrasound thermometry. Besides myocardium, the detection of hyperthermia around the ablation zone could be used to delimit the effective ablation area for other uses, such as neurologic or cancer therapy.

Ultrasound thermometry may be a useful tool in protecting the esophagus and/or lung structures such as the bronchus during ablation of atrial fibrillation through noninvasive temperature measurement of adjacent soft tissue. In addition, ultrasound thermometry may potentially be used for lesion assessment within the ablated tissue, although with potential technical difficulties (such as cardiac movement, and nonlinear acoustic and temperature relationships).

With particular reference to FIGS. 14-18, an ultrasound probe 20 according to five embodiments is described, the probes 20 are designed for three-dimensional acquisition with magnetic sensors 32 and/or electrodes 30 could be utilized within a three-dimensional mapping system such as a cardiac electrophysiology (EP) mapping system 45 (FIG. 13) to provide anatomical information, and/or specifically designed for ultrasound thermometry acquisition. One or more rows of piezoelectric crystals or other piezo sources 26, 27 could be arranged in parallel, for acquisition of multiple planes simultaneously through sensors 28, 29, with magnetic sensors 32 and/or electrodes 30 providing locational information for the three-dimensional mapping system. The probe 20 can also optionally include a standard temperature sensor 35 (FIGS. 14 and 15), such as a thermocouple, either for additional thermal monitoring/verification or for calibration or other normalization of data outputted by the system 10.

The multiple planes could be demonstrated as a true three-dimensional rendition of structure and ultrasound thermal mapping and/or multiple two dimensional images, which could be displayed through a three dimensional system such as a cardiac electrophysiology (EP) mapping system 45 and associated display 48. The catheter with the transducer can be deflectable (arrows X and Y of FIG. 14) through a deflectable point 23 at the tip 22 of the probe 20, distal of the trunk 24, and have a port within the catheter possibly for suction.

Balloon(s) can also be placed on the echo probe catheter (see FIG. 17) to improve contact of the ultrasound piezo source(s) 26, 28 and possibly to the esophagus E from the heart H. For an esophageal catheter, a balloon can be distal to the transducer, and proximal to the transducer, to isolate the area around the transducer, and a vacuum could be created to have the esophagus E collapse around the catheter. A port adjacent to the transducer can have suction capabilities to bring the esophagus tissue closer to the transducer, to improve tissue contact. Multiple ports can be present for esophagus manometry, suction, or drug delivery to reduce peristalsis (eg. Atropine).

An alternative probe 120 can be similar to the probe 20, but with the crystals or other ultrasound wave source provided in a pair and oriented longitudinally. In particular, a first longitudinal piezo source 126 and a second longitudinal piezo source can be provided, which are parallel with each other. Multiple parallel frames of data are thus efficiently acquired for three-dimensional data acquisition. Parallel longitudinal sensors 127, 129 would also be included.

Figure 16:
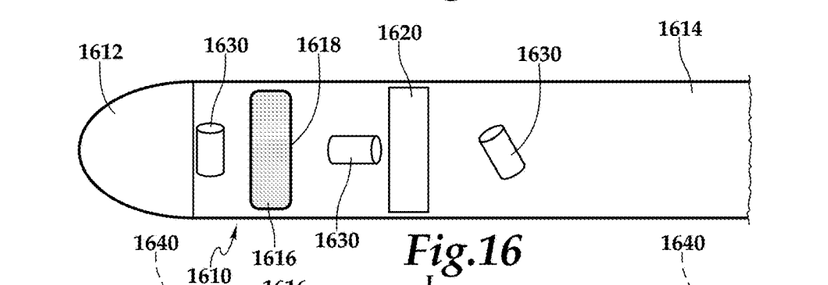
Figure 17:
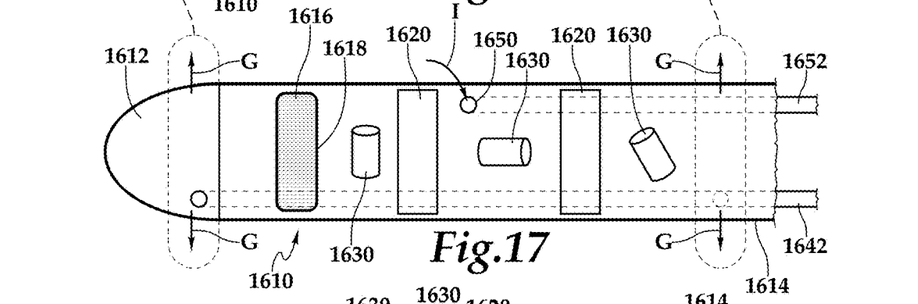
Figure 18:
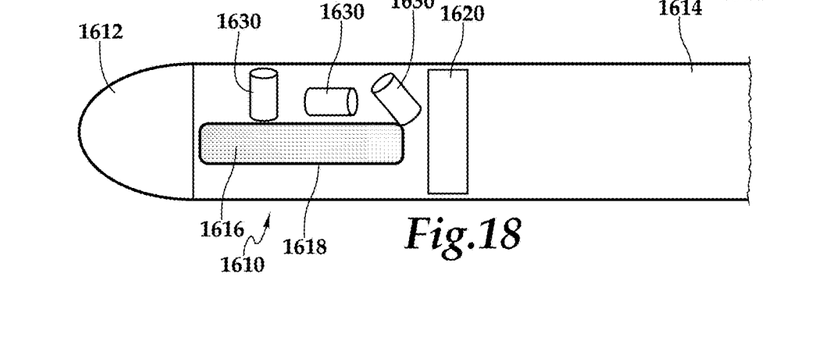

With particular reference to FIGS. 16-18, details of three other embodiments of probes 1610 are described. Such probes 1610 when adapted for use within the esophagus E could include a piezo source 1616 which could be lateral to a long axis of the probe 1610 (FIGS. 16 and 17) or parallel with a long axis of the probe 1610 (FIG. 18). The probe 1610 generally includes a tip 1612 at a distal end of a trunk 1614. A sensor 1618 can be provided, typically adjacent to the piezo source 1616, to detect the sonic radiation returning back after reflection off of bodily structures, and which signal associated with the sensor 1618 can be utilized to construct an ultrasound (or other) image. Such images, rather than being utilized for vascular access, would be utilized to protect the esophagus E and/or to otherwise assist in performing the intracardiac (or other intravascular) procedure.

In one embodiment depicted in FIG. 17, multiple electrodes 1620 are depicted on the probe 1610. The electrodes 1620 are parallel with each other and spaced longitudinally. Furthermore, magnetic field sensors 1630 are provided alone or along with the electrode (or electrodes 1620) such as for imaging within an EP mapping system 1320. In the embodiment depicted in FIG. 17 a balloon 1640 is provided adjacent to the tip 1612, and optionally a second balloon 1640 spaced from the tip 1612. The balloons 1640 can be expanded (along arrow G of FIG. 17), such as through provision of a fluid along a fill line 1642. These two balloons 1640 can be provided on either side of a region of the esophagus E to be protected. A suction port 1650 can be provided in the transesophageal echo probe 1610 between the balloons 1640, which is coupled to a vacuum line 1652 or other source of suction. When activated (drawing fluids along arrow I into the port 1650), walls of the esophagus E could be brought toward the probe 1610 to decrease a diameter of the esophagus E at an area of interest, and move the esophagus E away from the heart H, such as during an ablation procedure and to protect the esophagus E. Simultaneously, the probe 1610 can visualize walls of the esophagus E relative to walls of the heart H, such as to verify that spacing exists and to minimize damage, especially thermal damage to the esophagus E during performing of a cardiac ablation procedure.

The catheter can be pre-formed to promote tissue contact of the ultrasound transducer onto the esophagus surface (for example: Circular shaped, S-shaped, curved state or coil shaped). The catheter can be deflectable to allow for a relaxed state versus a preformed state. For example, the relaxed state allows for easy delivery into the esophagus E, while the preformed state promotes the tissue contact of the echo transducer. The preformed state could be an S-shaped curve, simple curve, or other shaped curve, coiled/helical, while the relaxed state is straight and flexible to allow for easy entry into the esophagus.

A lumen for a stylet which can be placed and/or replaced could also be present to improve tissue contact for the transducer. The stylet could be curved to shape the catheter and allow for improved tissue contact onto the surface of the esophagus. For example, the stylet could form the catheter into an S-shape curve or a coiled/helical curve. A catheter with or without a balloon also could be used, which also has suction capabilities to improve tissue contract (for example, like a vacuum cleaner which attaches to an object by suction). These additional enhancements to the esophageal catheter can also be applied to a standard two-dimensional echo esophageal catheter to favor tissue contact of the ultrasound transducer and ultrasound thermometry. The echo probe 20 or other ultrasound transducer can be transesophageal, transgastric, intravascular or externally such as transthoracic in origin.

Ultrasound thermometry could be applied in the clinical setting despite limitations in the range of temperature measurement and sensitivity to motion. Three-dimensional mapping systems such as cardiac electrophysiology (EP) mapping systems 45 are regularly used in clinical settings and can provide locational information of ultrasound probes 20 and consequently the ultrasound imaging window within a three-dimensional space. The capabilities of the three-dimensional mapping system can be leveraged to delineate tissue being ablated which achieves a threshold temperature within the three-dimensional space. Locational information of the transducer and the ultrasound window can be used for motion correction possibly in combination with a buffering algorithm, for increased accuracy in ultrasound temperature measurements. Finally, the ultrasound transducer can have multiple rows of crystals (or other ultrasound sources), possibly in different orientations mounted with electrodes 30 and/or magnetic sensors 32 for simultaneous visualization of multiple echo planes, to provide three-dimensional ultrasound data for the three-dimensional mapping system such as a cardiac electrophysiology mapping system.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When embodiments are referred to as "exemplary" or "preferred" this term is meant to indicate one example of the invention, and does not exclude other possible embodiments. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. A method for ablation of bodily structures while protecting adjacent tissues from damage, the method including the steps of:
    placing an ablation tool adjacent to a target bodily structure to be ablated;
    locating an ultrasound probe within range of tissues to be protected;
    operating the ablation tool to ablate the target bodily structure;
    evaluating ultrasound probe data during said operating step to determine temperature changes of tissues to be protected, based at least partially on detection of changes in speed of sound within the tissues to be protected, the speed change associated with temperature change; and
    adjusting said operating step when said evaluating step detects undesirable temperature change in the tissues to be protected.

2. The method of claim 1 wherein said operating step includes discharge of electric arc energy from the ablation tool.

3. The method of claim 1 wherein said operating step includes discharge of laser energy from the ablation tool.

4. The method of claim 1 wherein said operating step includes discharge of RF energy from the ablation tool.

5. The method of claim 1 wherein said operating step includes cryogenic heat transfer from the target bodily structure to the ablation tool to ablate by cooling the target bodily structure.

6. The method of claim 1 wherein said evaluating step includes displaying an image of tissues to be protected along with a visual indication of temperature of the tissues.

7. The method of claim 6 wherein the visual temperature indication of said evaluating step includes different colors indicative of different temperatures, the colors displayed upon the depiction of tissues to be protected.

8. The method of claim 6 wherein the visual temperature indication of said evaluating step is overlaid upon a display of an electrophysiology mapping system which is displaying tissues to be protected.

9. The method of claim 1 wherein said adjusting step includes the user pausing said operating step.

10. The method of claim 1 wherein said adjusting step includes the user moving the ablation tool away from tissues to be protected.

11. The method of claim 1 wherein said adjusting step includes decreasing a power level of the ablation tool.

12. The method of claim 11 wherein said decreasing step occurs automatically when a threshold temperature is detected in tissues to be protected according to a feedback loop.

13. The method of claim 12 wherein said decreasing step is terminated when temperature change in tissues to be protected drops below a desired maximum level of temperature change.

14. The method of claim 1 wherein the target bodily structure includes a portion of a patient's myocardium.

15. The method of claim 14 wherein the tissues to be protected include the esophagus.

16. The method of claim 15 wherein the tissues to be protected include an outer wall of the esophagus and said locating step includes locating the ultrasound probe within the esophagus.

17. The method of claim 15 wherein the tissues to be protected include the inner wall of the esophagus.

18. The method of claim 14 wherein the tissues to be protected include the pericardium.

19. The method of claim 14 wherein the tissues to be protected include lung tissues.

20. A method for ablation of bodily structures while protecting adjacent tissues from damage, the method including the steps of:
   placing an ablation tool adjacent to a target bodily structure to be ablated;
   viewing the target bodily structure with a three-dimensional mapping system;
   delineating tissue to be ablated within the mapping system;
   locating an ultrasound probe within range of tissues to be protected;
   operating the ablation tool to ablate the target bodily structure;
   evaluating ultrasound probe data during said operating step to determine temperature changes of the tissues to be protected, based at least partially on detection of changes in speed of sound within the tissues to be protected, the speed change associated with temperature change; and
   adjusting said operating step when said evaluating step detects undesirable temperature change in the tissues to be protected.

21. The method of claim 20, including the further step of correcting the ultrasound data from said evaluating step to compensate at least partially for motion.

22. The method of claim 21, including the further step of depicting temperature visually on a display associated with the three-dimensional mapping system.

* * * * *